United States Patent
Vija et al.

(10) Patent No.: US 11,151,759 B2
(45) Date of Patent: Oct. 19, 2021

(54) DEEP LEARNING-BASED DATA RESCUE IN EMISSION TOMOGRAPHY MEDICAL IMAGING

(71) Applicant: Siemens Medical Solutions USA, Inc., Malvern, PA (US)

(72) Inventors: Alexander Hans Vija, Evanston, IL (US); Michal Cachovan, Baiersdorf (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 142 days.

(21) Appl. No.: 16/564,511

(22) Filed: Sep. 9, 2019

(65) Prior Publication Data

US 2021/0074033 A1    Mar. 11, 2021

(51) Int. Cl.
| | |
|---|---|
| *G06T 11/00* | (2006.01) |
| *A61B 6/03* | (2006.01) |
| *G01T 1/164* | (2006.01) |
| *G06N 20/00* | (2019.01) |

(52) U.S. Cl.
CPC ............ *G06T 11/005* (2013.01); *A61B 6/037* (2013.01); *G01T 1/164* (2013.01); *G06T 11/006* (2013.01); *A61B 6/032* (2013.01); *G06N 20/00* (2019.01); *G06T 2211/424* (2013.01)

(58) Field of Classification Search
None
See application file for complete search history.

(56) References Cited

U.S. PATENT DOCUMENTS

| | | | |
|---|---|---|---|
| 8,483,460 B2 | 7/2013 | Malmin | |
| 2015/0170055 A1* | 6/2015 | Beymer | G06N 20/00 706/12 |
| 2017/0213355 A1* | 7/2017 | Hujsak | H01J 37/222 |

OTHER PUBLICATIONS

Felix Nensa, et al. "Artificial Intelligence in Nuclear Medicine" The Journal Of Nuclear Medicine. vol. 60 No. 9. Sep. 2019. pp. 29S-37S.

Mathieu Hatt, et al. "Radiomics: Data Are Also Images" The Journal Of Nuclear Medicine. vol. 60 No. 9. Sep. 2019. pp. 38S-44S.

\* cited by examiner

*Primary Examiner* — Edwin C Gunberg

(57) ABSTRACT

An emission image is generated from poor quality emission data. A machine-learned model may be used to recover information. Emission imaging may be provided due to the recovery in a way that at least some diagnostically useful information is made available despite corruption that would otherwise result in less diagnostically useful information or no image at all.

20 Claims, 2 Drawing Sheets

10 — Obtain Nuclear Imaging Data Failing Scan Guideline

12 — Recover Information from Nuclear Imaging Data with Machine-Learned Model

14 — Generate Image with the Recovered Information

DEEP LEARNING-BASED DATA RESCUE IN EMISSION TOMOGRAPHY MEDICAL IMAGING

BACKGROUND

The present embodiments relate to emission tomography imaging. Emission tomography imaging includes single photon emission computed tomography (SPECT) and positron emission tomography (PET) imaging. Emission tomography imaging uses a radioisotope or radiotracer to determine physiological function within a patient. A spatial distribution of the radioisotope is imaged based on counts of emissions from the radioisotope or radiotracer in the patient.

To scan the patient, the patient is placed in a bore and asked to limit movement over many minutes. The scan proceeds until sufficient data for imaging is acquired. A clinical guideline for scan quality may indicate the scan process and corresponding time to acquire sufficient data. For various reasons, the scan may not be completed or may result in corrupted data that does not satisfy the guideline. For example, a patient may panic and remove themselves from the bore or may move a substantial amount within the bore. Where the scan does not satisfy the guideline, the scan may need to be repeated or the desired imaging may not be provided due to data corruption. The corruption, such as due to an incomplete scan, may lead to images that are not diagnostically useful.

SUMMARY

By way of introduction, the preferred embodiments described below include methods, systems, and non-transitory computer readable media for generating an emission image from poor quality emission data. A machine-learned model may be used to recover information. Emission imaging may be provided due to the recovery in a way that at least some diagnostically useful information is made available despite corruption that would otherwise result in less diagnostically useful information or no image at all.

In a first aspect, a method is provided for generating a nuclear image from poor quality data of a medical nuclear imaging system. Nuclear imaging data that fails to satisfy a guideline for scan quality is obtained. The nuclear imaging data represents emissions from a patient. Information is recovered from the nuclear imaging data. The information is output by a deep machine-learned model in response to input of the nuclear imaging data. The nuclear image of the patient is generated from the recovered information.

The nuclear imaging data may be positron emission tomography data or single photon emission computed tomography data. The data are from any point in the scan or processing path, such as measured counts or projection data along lines of response or reconstructed data representing a volume or plane.

Various embodiments are provided for to what extent the nuclear imaging data is corrupted. The nuclear imaging data may have insufficient quality to invert a Radon transform. The nuclear imaging data may be at least 25% below a Nyquist criteria. The nuclear imaging data may be SPECT data with an orbit of a gamma camera 10% or more incomplete. The nuclear imaging data may be insufficient to the point that iterative reconstruction fails.

In one embodiment, the nuclear imaging data is obtained as first projection data from the emissions. The information is recovered as second projection data. The nuclear image is generated from the first and second projection data.

In another embodiment, the nuclear imaging data is obtained as first reconstructed data. The information is recovered as second reconstruction data. The image is generated from the first and second reconstruction data.

In yet another embodiment, the nuclear imaging data is obtained as forward or backward projection data in an objective function as part of reconstruction. The information is recovered as part of the reconstruction.

Translation may be used. For example, the information is output by the deep machine-learned model in response to the input of the nuclear imaging data and x-ray, computed tomography, ultrasound, or magnetic resonance data.

Multiple models may be used. For example, the deep machine-learned model is selected from a group of deep-machine learned models. Each of the models of the group is different. Different types of machine learning and/or corresponding machine-learned models may work better than others in different situations. In one embodiment, each of the models of the group is applied. A better performing one of the models of the group is selected for recovering from the obtained nuclear imaging data.

In one embodiment, the deep machine-learned network was trained with training data samples created by artificial corruption. The samples without the artificial corruption are the ground truth data.

In a second aspect, a system is provided for recovering from an suboptimal or corrupted multi-modal emission tomography scan. An emission tomography scanner is configured to scan a patient, the scan of the patient resulting in suboptimal or corrupted data. A medical imager is configured to scan the patient with ultrasound, x-ray, or radio frequency transmissions, the scan providing imager data. A processor is configured to generate additional data as output by a machine-learned model in response to input of the suboptimal or corrupted data and the imager data. The processor is configured to form an emission image from the suboptimal or corrupted data and the additional data. A display is configured to display the emission image.

In one embodiment, the suboptimal or corrupted data is data failing to satisfy a clinical guideline for scan quality or having a sampling at least 10% below Nyquist for at least a region of the patient.

In another embodiment, the processor is configured to select the machine-learned model from a plurality of machine-learned models. In a further embodiment, the processor is configured to apply the machine-learned models of the plurality to the suboptimal or corrupted data and select the machine-learned model to output the additional data based on the application.

Various types of machine-learned models may be used. In one embodiment, the machine-learned model is a deep learned neural network.

In a third aspect, a method is provided for training for rescue of medical information from an emission tomography scan by an emission tomography scanner. A plurality of ground truth emission tomography data sets is acquired. The emission tomography data is corrupted by removing one or more views, sub-sampling, or truncating such that the emission tomography data is below a Nyquist rate for at least a part. A network is machine trained to generate the medical information from the corrupted emission tomography data based on the ground truth emission tomography data. The machine-trained network is stored.

In one embodiment, the network is machined trained to generate the medical information from the corrupted emission tomography data and data from another modality of imaging.

The present invention is defined by the following claims, and nothing in this section should be taken as a limitation on those claims. Features, embodiments, or aspects of one type of claim (e.g., method or system) may be used in another type of claim (e.g., system or method). Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Medically relevant information is rescued from a suboptimized or corrupted emission tomography scan. In one embodiment, the medically relevant information is rescued using multi-modal scanning. Translation from one modality to an emission modality may be used.

One or different deep learning approaches are used for artifact reduction, noise reduction, an/or replacing missing data to recover as much information as possible. For machine training, a training dataset of uncorrupted data is used to artificially create corrupted data. The machine learning uses the uncorrupted data as ground truth data and the artificially created corrupted data as the input samples.

Figure 1:
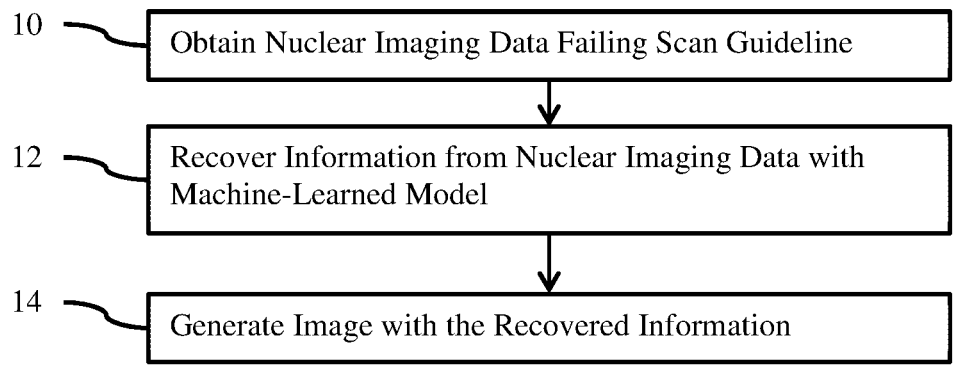
FIG. 1 is a flow chart diagram of one embodiment of a method for generating a nuclear image from poor quality data of a medical nuclear imaging system.

FIG. 1 shows one embodiment of a method for generating an image from poor quality data of a medical nuclear imaging system. A machine-learned model generates additional information from the poor-quality data. The poor-quality data with the additional information may be used to generate a nuclear image where the poor-quality data alone cannot and/or may be used to generate a nuclear image with more or even some diagnostic information. For example, where a patient exits the imaging system before ½ of an emission scan is complete, some diagnostically useful information may still be recovered.

Figure 3:
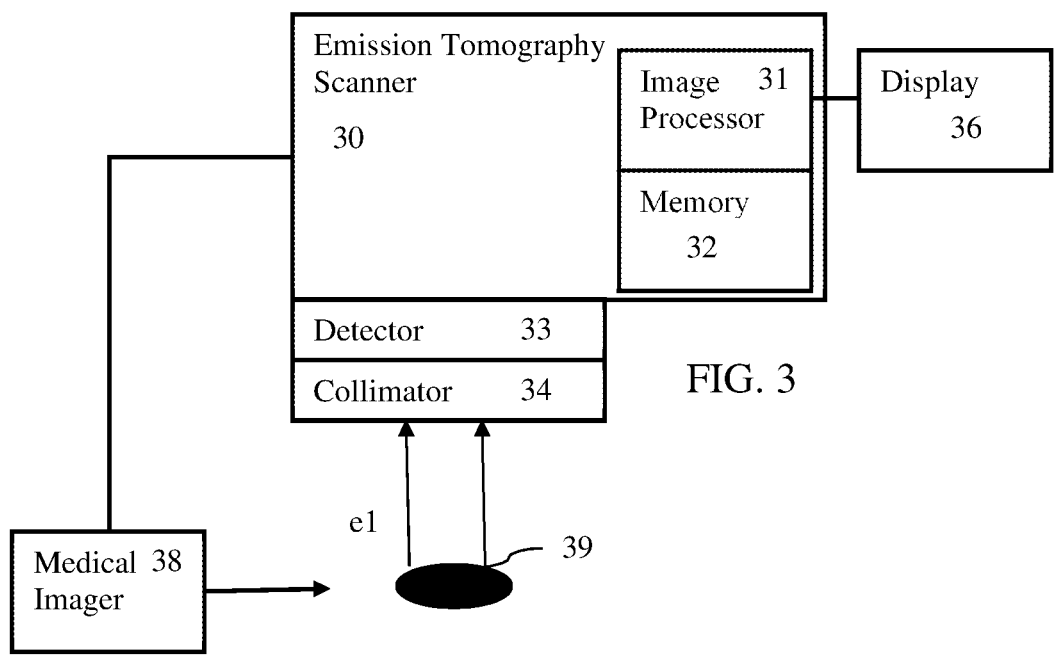
FIG. 3 is a block diagram of a system, according to one embodiment, for recovering from a suboptimal or corrupted multi-modal emission tomography scan.

The system of FIG. 3 or a different system performs the method. For example, an image processor, interface, memory, and/or emission tomography system obtain the data. An image processor recovers, and the image processor with a display displays a nuclear image. Other devices may perform any of the acts.

Additional, different, or fewer acts may be performed. For example, acts related to positioning the patient, configuring the nuclear imaging scanner, rotating the detector about the patient, and/or imaging are provided. The acts are performed in the order shown or a different order.

In act 10, a medical nuclear scanner obtains nuclear imaging data. The nuclear imaging data represents emissions from a patient. For example, a PET or SPECT system obtains nuclear imaging data (e.g., obtaining PET data or SPECT data). The nuclear scanner detects emissions from a patient. After ingesting or injecting the radiotracer into the patient, the patient is positioned relative to a gamma camera (e.g., SPECT camera) or a ring or cylinder of detectors (e.g., PET detector). The detectors or camera are positioned relative to the patient. Emissions from the radiotracer within the patient are detected over time. A collimator limits the direction of emissions detected, so each detected emission is associated with an energy and line or cone of possible locations from which the emission occurred. The lateral position of the line or cone relative to the detector may likewise be determined. For SPECT, the detector may be rotated or moved relative to the patient, allowing detection of emissions from different angles and/or locations in the patient.

In alternative embodiments, the nuclear imaging data is obtained from transfer in a computer network. Data from a previous scan is transferred. In other embodiments, the nuclear imaging data is obtained by loading from memory.

The nuclear imaging data is data from the emission tomography processing pipeline. The imaging data is data that may be used to generate an image or data that is an image. For example, the nuclear imaging data are measurements from the detectors, such as projection data representing energy and/or count per line of response. As another example, the nuclear imaging data is data for forward or backward projection as part of reconstruction (e.g., tomography), such as being data for the objective function used in iterative reconstruction. In yet other embodiments, the data is reconstructed data representing spatial locations in object space, such as data representing a volume.

The nuclear imaging data fails to satisfy a guideline for scan quality. The patient includes a radiotracer with an isotope emitting energy. The emissions are collimated and detected using a scan protocol. The scan protocol includes a guideline for scan quality to adequately sample the patient for reliable reconstruction and diagnostic emission tomography imaging. The guideline provides for sampling satisfying the Nyquist criterion, sufficient data to invert a Radon transform, and/or sufficient data to allow for iterative reconstruction. Iterative reconstruction may be performed with some data is missing, such as being within 10% of the Nyquist criterion. Lesser sampling may result in the inability to reliably reconstruct. In a SPECT example, the guideline calls for the gamma camera or a dual camera system to rotate at least 180 degrees around the patient. If the patient leaves early, a lesser rotation and incomplete sampling results. For example, the gamma camera or cameras are rotated only 45, 90, 120, or other number of degrees (e.g., less than 75% of the planned rotation of the guideline).

The nuclear imaging data may be obtained with insufficient quality. The insufficient quality results in corrupted or suboptimal data. The insufficient quality may be such that the data cannot be used to invert a Radon transform. The nuclear imaging data may be subsampled by at least 25% below a Nyquist criteria for at least part of the scan or representation of the patient. The range of motion, such as rotation of a gamma camera and/or lateral translation of the patient relative to the scanner, may be 10% or more incomplete. The insufficient quality may be such that iterative reconstruction fails. The reconstruction may not meet one or more thresholds for quality, such as artifacts, noise level, or truncation measurements.

In act 12, the image processor recovers information from the nuclear imaging data. The recovered information fills in some of the missing information to counteract at least part of the insufficient quality. Gaps in data are filled and/or data is corrected.

The recovered information is a recovering of what is missing due to the poor-quality scan, such as recovering missing projection data, missing data used in reconstruction, and/or missing reconstructed data. Data to fill gaps is recovered in the sense of creating data that was not obtained due to incomplete scanning relative to the guideline. Values of the data may be changed as part of recovery.

The recovery is performed by a machine-learned model. Machine training is used to learn to recover from an incomplete scan in order to provide more useful diagnostic information without requiring rescanning of the patient. The machine-learned model outputs the information or a combination of the information and the input incomplete nuclear imaging data in response to input of the incomplete nuclear imaging data.

Figure 2:
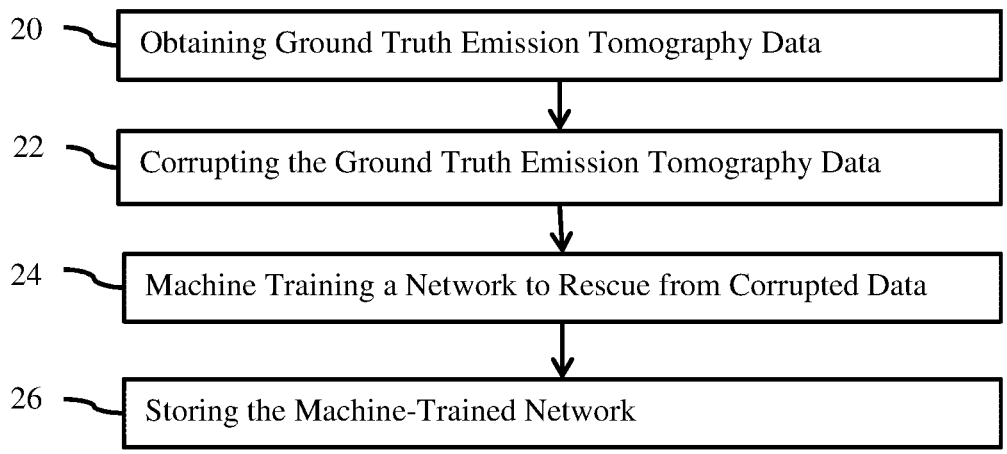
FIG. 2 is a flow chart diagram of one embodiment of a method for training for rescue of medical information from an emission tomography scan by an emission tomography scanner.

FIG. 2 shows one embodiment of a method for training for rescue of medical information from an emission tomography scan by an emission tomography scanner. Machine learning, such as deep machine learning for a neural network, trains a model (e.g., neural network) to recover information from an insufficient emission tomography scan. The machine-learned model is trained with training data samples created by artificial corruption of ground truth nuclear imaging data.

FIG. 1 is directed to application of the machine-learned model. FIG. 2 is directed to training of the machine-learned model to then be used in application.

The acts of FIG. 2 are performed by the system of FIG. 3 or a different system. For example, a server, workstation, computer, image processor, or other processor performs the machine training and uses a memory to store the machine-learned model. The same or different processor and/or nuclear imaging system are used to generate the training data. The same or different nuclear imaging system may use the machine-learned model. Other devices may perform any of the acts.

Additional, different, or fewer acts may be performed. For example, act 26 is not provided. As another example, acts 20 and 22 are not performed where the training data is already provided. In yet another example, acts related to configuring an architecture of the model for machine training are provided. The acts are performed in the order shown or a different order.

In act 20, an image processor obtains a plurality of ground truth emission tomography data. The emission tomography data is nuclear imaging data, such as data obtained by sufficient or complete PET or SPECT scans. Scans that satisfy the scan quality guideline are obtained as ground truth projection data, objective function data in or as part of reconstruction, or reconstructed data. In an alternative embodiment, physics simulation is used to create the ground truth emission tomography data. The nuclear imaging is simulated.

The training data includes tens, hundreds, or thousands of samples. Each sample includes input data and ground truth data. The machine training learns from the samples to estimate an output from the input. The ground truth data is the desired output given the input. By comparing estimates output by the machine-learned model given the input to the ground truth, the machine learning alters the programmable parameters of the model to best predict the output given an unseen input.

In act 22, the image processor corrupts the emission tomography data. The input data is artificially created from the ground truth nuclear imaging data. The nuclear imaging data is altered to emulate an insufficient scan. The input data of the training data is formed from the ground truth. For each sample of the desired or ground truth output to be used in machine learning, one or more corrupted forms of the nuclear imaging data are created.

Different amounts and/or types of corruption may be applied to each ground truth sample. One ground truth may be used to create one or more pairs of the corrupted data and the ground truth data. By corrupting by different amounts, different locations, and/or different types, different sample pairs of input and ground truth output data are created.

Various alterations may be applied. For example in SPECT, the data for one or more views (i.e., given positions for the gamma camera) are removed. As another example, counts for one or more ranges of time are removed. Other examples include sub-sampling over all the data, sub-sampling different parts by different amounts, and/or sub-sampling only part of the nuclear imaging data. Yet another example is truncating the data, such as removing a block of data. The truncation may be by time, such as to emulate a scan starting but not being finished. Other alterations that emulate insufficient emission tomography scanning may be used.

The corruption may result in data below a Nyquist rate for at least a part or all of the scan or dataset from the scan. The corruption provides training data not meeting any one, more, or all of the measures of sufficiency.

In act 24, a machine (e.g., the image processor) machine trains a model to generate the medical information from the corrupted emission tomography data based on the ground truth emission tomography data. The model, such as a neural network, includes learnable parameters, the values of which are determined in machine training to output recovered information from an input of corrupted or insufficient data. For example, the machine training determines the values of the learnable parameters (e.g., weights, connections, filter kernels, pooling, . . . ) that estimate missing data as medical information.

In one embodiment, deep learning is used. A neural network (e.g., deep learning) arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

Deep architectures include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through back-propagation. DBN, on the other hand, employs layer-wise unsupervised training (e.g., pre-training) followed by the discriminative refinement with back-propagation if necessary. In one embodiment, a CNN, such as a fully convolutional neural network, is used.

Any neural network architecture may be used, such as an image-to-image or generative network. The architecture is the arrangement of layers for the network. In one embodiment for registration, a convolutional-transposed-convolutional network is used. One segment of layers or units applies convolution to increase abstractness or compression. The most abstract feature values are then output to another segment. The other segment of layers or units then applies transposed-convolution to decrease abstractness or compression, resulting in outputting of an image or multi-channel data. In a further embodiment, the neural network is a U-net. An encoder (convolutional) and decoder (transposed-convolutional) network forms a "U" shape with one vertical being encoding, another vertical being decoding, and the connection between being passing features at a greatest level of compression or abstractness from the encoder to the decoder. Other fully convolutional networks may be used. The U-net may include skip connections, such as passing values for features at any level of abstractness from the encoder to the corresponding level of the decoder.

In other embodiments, a DenseNet is used. Any arrangement of layers relating input information to the output may be used. A multi-channel input (e.g., one channel for each characteristic of the arrangement) and a multi-channel output (e.g., one channel for each parameter of the noise model) with any number of intervening layers is provided. A generative adversarial network may be used. An image-to-image, encoder-decoder, or another network architecture may be used.

The machine (e.g., image processor) trains the defined neural network arrangement. The training data samples and ground truths are used to train the neural network. One network is trained to output more complete or sufficient nuclear imaging data given input of corrupted or insufficient data.

In training, the similarity of the estimated nuclear imaging data to the ground truth is minimized. For example, the neural network is trained as a regression problem with the sum-of-squared differences loss. Other loss functions, such as L1, L2, or Huber may be used. Any optimization may be used, such as Adam, RMSprop optimizer, or SGD. Batch normalization, dropout, and data augmentation may be used. During the optimization, the different distinguishing features of the input data are learned. The features providing an indication of recovered data are learned.

In alternative embodiments, other machine learning and corresponding models may be used. For example, a support vector machine is used.

Other input data may be used in addition to the corrupted data. For example, data for modality translation is provided. For each sample of training data, image data (e.g., scan or reconstructed data) from a different modality is input. The other modality data represents the patient of the sample over a same, smaller, or greater region of the patient. Any modality may be used, such as ultrasound, x-ray, computed tomography, or magnetic resonance. The input sample is the image data from one modality and the insufficient or corrupted emission tomography data. The machine learning learns to output medical information in the form of missing emission tomography or nuclear imaging data based on input of the insufficient emission tomography or nuclear imaging data and the imaging data of the other modality.

In act 26, the machine (e.g., image processor) outputs a trained neural network or machine-learned model. In the deep learning example, the machine-learned model incorporates the deep learned features for the various units and/or layers of the network. The values for the learnable parameters of the architecture result from training. The architecture and the values of the learnable parameters are output as the machine-learned network or model.

Once trained, a matrix, kernels (e.g., learned convolution weights), or other trained network or model is output. The data represents the trained architecture.

The machine-learned model is output to a computer network or memory. For example, the neural network as trained is stored in a memory for transfer and/or later application.

Returning to FIG. 1, the machine-learned model is applied to the poor-quality nuclear imaging data. The machine-learned model outputs the recovered information in response to the input of the poor-quality nuclear imaging data. In the modality translation or multi-modality embodiment, the machine learned model outputs the information in response to input of the poor quality nuclear imagining data and the data representing the patient from the other modality (e.g., x-ray, computed tomography, ultrasound, or magnetic resonance data).

In one embodiment, a plurality of models is machine learned. For example, different models are trained to receive different types, amounts, and/or locations of corruption. In application, the user selects the appropriate one of the different machine-learned models. Alternatively, the nuclear imaging data from the scan of the patient is image processed to select the machine-learned model to use by the image processor.

In yet another embodiment, a sub-set or all of the models are used. The insufficient or poor-quality nuclear imaging data from the scan of the patient is input to multiple machine-learned models. The resulting output information, combination of output information and the input nuclear imaging data, or images generated from the output information of the different machine-learned models are compared. Based on user visual comparison and/or image processing, a better performing model and corresponding output are selected for use in imaging. The performance may be rated in various ways, such as distance or difference from template for emission tomography data for the region being scanned.

In act 14, the image processor generates a nuclear image of the patient from the recovered information. The recovered information alone or in combination with the input nuclear imaging data is used to generate the nuclear image.

In one embodiment, the recovered information is projection data. The combined projection data from the output of the machine-learned network and the input poor quality projection data are used to generate an image. Tomography, such as computed tomography, is used to reconstruct the nuclear image from the projection data. The projection data represents the detected emissions. A processor of the nuclear imaging system reconstructs the image or object that represents the emission distribution in the patient. The quantity or amount of uptake for each location (e.g., voxel) may be estimated as part of the reconstruction. The nuclear imaging system estimates the activity concentration of an injected radiopharmaceutical or tracer for the different locations.

Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, non-negative least squares (NNLS), or another approach. Any models and/or compensation (e.g., motion compensation) may be used in the reconstruction.

The reconstruction is iterative. The iterative reconstruction forward projects a current estimate of the volume or image (e.g., object space) to projection space using forward projectors representing the detection. Since the detected emissions are in a projection space (e.g., generally known location in two-dimensions but not three dimensions), the forward projection of the current volume is compared to the detected or measured emissions. This comparison is tested for accuracy with a merit function (e.g., ML-EM or NNLS). If sufficiently accurate and/or having no further increase in accuracy, the iteration ceases, and the current volume is output as the reconstructed volume. If the merit function indicates insufficient or improving accuracy, a difference between the forward projection and the detected emissions is backward projected. This backward projection provides a gradient or change for the volume. The direction and step size are determined for the change and applied to update the volume. The process is then repeated for another iteration of the reconstruction.

In another embodiment, the objective function, such as the backward or forward projection data, is estimated by the machine-learned model. The reconstruction receives the insufficient nuclear imaging data as projection data for input. The reconstruction is performed iteratively on that data. Some of the data used in the reconstruction (i.e., within the iteration process), such as forward or backward projected data, is estimated as the medical information by the machine-learned model based on input of data from the insufficient projection data. The machine-learned model outputs data used within iteration in the reconstruction rather than outputting projection data or reconstructed data.

Once the reconstruction is complete, an image is generated from the reconstruction data. In another embodiment, reconstruction is performed on the insufficient projection data. The machine-learned model receives as input the reconstruction data as the nuclear imaging data. The machine-learned model outputs medical information in the object domain, such as additional data for the reconstruction. The additional data is for different locations and/or for a change in amplitude for a given location (i.e., voxel or pixel). The image is generated from reconstruction data from the insufficient scan and reconstruction data output by the machine-learned model.

The image processor generates an image from the reconstruction data. For example, a qualitative PET or SPECT image is generated. As another example, a quantitative PET or SPECT image is generated. Due to the machine-learned model-based medical information, the image more likely represents the patient and/or provides more diagnostic information than without the additional medical information.

A nuclear image of the patient or part of the patient is generated from the reconstruction or representation. The results of the reconstruction represent a distribution of emissions or counts of emissions in three-dimensions. For qualitative emission imaging, this distribution is used to generate an image. For quantitative emission imaging, the activity concentration for each location (e.g., voxel) is determined.

The nuclear image is generated from the reconstructed object (e.g., whole patient or part of the patient). In one embodiment, data for one or more (e.g., multi-planar reconstruction) planes is extracted (e.g., selected and/or interpolated) from a volume or voxels and used to generate a two-dimensional image or images. In another embodiment, a three-dimensional rendering is performed. Projection or surface rendering is used to create a representation of the volume or part of the patient from a given viewing direction on the two-dimensional screen.

In one embodiment, the image is annotated. The annotation indicates that the scan was insufficient, and that the image is an estimate based on the insufficient scan. An anatomical image may be displayed with the nuclear image. For example, an emission tomography image is displayed alone, adjacent to a computed tomography (CT) image, or overlaid on a CT image (e.g., color for emission tomography and grayscale for computed tomography). Multi-modality images with magnetic resonance, ultrasound, x-ray, or other modalities may be used.

FIG. 3 shows a system for recovering from a suboptimal or corrupted multi-modal emission tomography scan. The system is a PET, SPECT, or other emission tomography system. The system implements the method of FIG. 1, FIG. 2, or another method.

The system includes an emission tomography scanner 30, an image processor 31, a memory 32, and a display 36. The image processor 31, memory 32, and/or display 36 are part of the emission tomography scanner 30 or are separate (e.g., a computer or workstation). The system may include a medical imager 38.

Additional, different, or fewer components may be provided. For example, the system is a computer without the emission tomography scanner 30. As another example, user input, patient bed, or other emission tomography related devices are provided. Other parts of the system may include power supplies, communications systems, and user interface systems.

The emission tomography scanner 30 is a PET, SPECT, or another emission tomography scanner. In general, the scanner 30 includes a detector 33 and a collimator 34. Other components may be provided. Any now known or later developed emission tomography scanner 30 may be used.

For SPECT, the detector 33 is one or more gamma cameras connected with a gantry. The gamma camera is a planar photon detector, such as having crystals or scintillators with photomultiplier tubes or another optical detector. The gantry rotates the gamma camera about the patient. During scanning of a patient, emission events are detected with the camera at different positions or angles relative to the patient. For PET, the detector 33 is a ring or cylinder of detectors forming a bore in which the patient rests during detection. Pairs of events on spaced apart detectors are matched to detect an emission.

The collimator 34 is a lead or other material forming a grid of holes. The collimator 34 may be moveable and/or configurable, such as by moving plates. In other embodiments, the collimator 34 is fixed relative to the detector 33.

The emission tomography scanner 30, using the detector 33 and collimator 34, detects emissions from the patient 39 for measuring uptake or physiological function. The detector 33 detects emissions at an energies range, el, from the patient 39. The energy ranges correspond to energy of the isotope in the patient. For imaging uptake in a patient, the detector 33 detects emissions from the patient. The emissions occur from any location in a finite source (i.e., the patient). The radiotracer in the patient migrates to, connects with, or otherwise concentrates at specific types of tissue or locations associated with specific biochemical reactions. As a result, a greater number of emissions occur from locations of that type of tissue or reaction.

The detector 33 applies one or more energy thresholds or other process to detect emission energy at a given energy range. The emissions for the energy range are counted.

For SPECT, the detector 33 and collimator 34 may be moveable with respect to the patient 39. The detector 33 and collimator 34 may continuously move or may be positioned at different locations for particular times. Alternatively or additionally, a patient bed moves the patient 39 relative to the detector 33 and collimator 34.

The emission tomography scanner 30 is configured to scan a patient. The patient 39 with the radiotracer is positioned relative to the detector 33. A scan protocol defining the time at each relative position of the detector 33 to the patient, energy thresholds, and/or other settings of the scanning is followed.

The scan protocol may not be followed. As a result, the scan of the patient results in suboptimal or corrupted data. For example, data failing to satisfy a clinical guideline for scan quality or having a sampling at least 10% below Nyquist for at least a region of the patient is acquired from the scanning.

The medical imager 38 is an x-ray, ultrasound, computed tomography, magnetic resonance, or another imager of a different modality than the emission tomography scanner 30. The medical imager 38 is configured by settings to scan the patient with ultrasound, x-ray, or radio frequency transmissions. Imager data in addition to the emission tomography data is provided. In alternative embodiments, the medical imager 38 and corresponding data is not provided, or the medical imager data is obtained from memory, such as from a previous scan of the patient.

The image processor 31 is a general processor, artificial intelligence processor or accelerator, digital signal processor, graphics processing unit, application specific integrated circuit, field programmable gate array, digital circuit, analog circuit, combinations thereof, or other now known or later developed device for processing emission information and/or applying a machine-learned model. The image processor 31 is a single device, a plurality of devices, or a network. For more than one device, parallel or sequential division of processing may be used. Different devices making up the image processor 31 may perform different functions, such as one processor (e.g., application specific integrated circuit or field programmable gate array) for reconstructing, another for applying the machine-learned model (e.g., control or general processor), and yet another (e.g., graphics processing unit) for generating an image. In one embodiment, the image processor 31 is a control processor or other processor of emission tomography scanner 30. In other embodiments, the image processor 31 is part of a separate workstation or computer.

The image processor 31 operates pursuant to stored instructions to perform various acts described herein. The image processor 31 is configured by software, firmware, and/or hardware to perform the acts.

The image processor 31 is configured to generate additional data as output by a machine-learned model in response to input of the suboptimal or corrupted data and/or the imager data. For example, a deep learned neural network generates projection data, data for the objective function in reconstruction, and/or reconstruction data to replace and/or fill-in the suboptimal or corrupted data.

In one embodiment, the image processor 31 is configured to select the machine-learned model from a plurality of machine-learned models. Different models are trained in different ways, with different training data, and/or with different architectures, so perform or operate to generate different additional data for a same input. The machine-learned model trained for the particular situation is selected. Alternatively, multiple of the machine-learned are applied by the image processor 31, and the results of the applications are used to select, such as testing images generated using the additional data and selecting one of the images and corresponding machine-learned models.

The image processor 31 is configured to reconstruct a volume or object from projection data. The emission tomography scanner 30, using the image processor 31 or another processor, is configured to reconstruct the imaged volume from the detected data (i.e., projections). Any reconstruction may be used to estimate the activity concentration or distribution of the tracer in the patient. The emission tomography scanner 30 accesses the detected emission events from the memory 32, from the detector 33, or buffers to reconstruct. The detected emissions are used to reconstruct the distribution of the radioisotope in three dimensions. Forward and backward projection are used iteratively until a merit function indicates completion of the reconstruction.

The image processor 31 is configured to form an emission image from the suboptimal or corrupted data and the additional data. The projection data, data generated in forward and/or backward projection in reconstruction, and/or reconstructed data includes the additional data generated by the machine-learned model. The reconstructed data includes information from the additional data. As a result, the image includes information from the additional data so that the image provides more diagnostic information than if the machine-learned model did not provide the additional data. The image shows the spatial distribution, such as with a multi-planar reconstruction or a volume rendering.

The display 36 is a CRT, LCD, plasma screen, projector, printer, or other output device for showing or display of an emission image. The display 36 displays an image of the reconstructed functional volume, such as showing activity concentration as a function of location. Alternatively or additionally, any quantities derived by the image processor 31 may be displayed.

The memory 32 is a buffer, cache, RAM, removable media, hard drive, magnetic, optical, database, or other now known or later developed memory. The memory 32 is a single device or group of two or more devices. The memory 32 is part of emission tomography scanner 30 or a remote workstation or database, such as a PACS memory.

The detected emission events, projection data, data used in reconstruction, reconstructed data, additional data, corrupted or suboptimal data, or other emission tomography information are stored in the memory 32. The memory 32 may store data at different stages of processing, such as counts, raw data representing detected events without further processing, filtered or thresholded data prior to reconstruction, forward projections, backward projections, differences, projection operators, transposed operators, a measure of completeness of reconstruction, reconstructed data, filtered reconstruction data, thresholds, results of calculations, an image to be displayed, an already displayed image, or other data. The data is stored in any format.

The memory 32 is additionally or alternatively a non-transitory computer readable storage medium with processing instructions. The memory 32 stores data representing instructions executable by the programmed image processor 31. The instructions for implementing the processes, methods, and/or techniques discussed herein are provided on non-transitory computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for generating a nuclear image from poor quality data of a medical nuclear imaging system, the method comprising:
   obtaining nuclear imaging data that fails to satisfy a guideline for scan quality, the nuclear imaging data representing emissions from a patient;
   recovering information from the nuclear imaging data, the information output by a deep machine-learned model in response to input of the nuclear imaging data; and
   generating the nuclear image of the patient from the recovered information.

2. The method of claim 1 wherein obtaining comprises obtaining the nuclear imaging data with insufficient quality to invert a Radon transform.

3. The method of claim 1 wherein obtaining comprises obtaining the nuclear imaging data at least 25% below a Nyquist criteria.

4. The method of claim 1 wherein obtaining comprises obtaining single photon emission computed tomography data with an orbit of a gamma camera 10% or more incomplete.

5. The method of claim 1 wherein obtaining comprises obtaining the nuclear imaging data for which iterative reconstruction fails.

6. The method of claim 1 wherein obtaining the nuclear imaging data comprises obtaining first projection data from the emissions, wherein recovering comprises recovering the information as second projection data, and wherein generating comprises generating the image from the first and second projection data.

7. The method of claim 1 wherein obtaining the nuclear imaging data comprises obtaining first reconstructed data, wherein recovering comprises recovering the information as second reconstruction data, and wherein generating the image comprises generating the image from the first and second reconstruction data.

8. The method of claim 1 wherein obtaining the nuclear imaging data comprises obtaining forward or backward projection data in an objective function as part of reconstruction, and wherein recovering comprises recovering the information as part of the reconstruction.

9. The method of claim 1 wherein obtaining the nuclear imaging data comprises obtaining positron emission tomography data or single photon emission computed tomography data.

10. The method of claim 1 wherein recovering comprises recovering where the information is output by the deep machine-learned model in response to the input of the nuclear imaging data and x-ray, computed tomography, ultrasound, or magnetic resonance data.

11. The method of claim 1 wherein recovering comprises selecting the deep machine-learned model from a group of deep-machine learned models, each of the models of the group being different.

12. The method of claim 11 wherein selecting comprises applying each of the models of the group, the recovering being a better performing one of the models of the group for recovering from the obtained nuclear imaging data.

13. The method of claim 1 wherein the deep machine-learned network was trained with training data samples created by artificial corruption, the samples without the artificial corruption comprising the ground truth data.

14. A system for recovering from suboptimal or corrupted multi-modal emission tomography scan, the system comprising:
   an emission tomography scanner configured to scan a patient, the scan of the patient resulting in suboptimal or corrupted data;
   a medical imager configured to scan the patient with ultrasound, x-ray, or radio frequency transmissions, the scan providing imager data;
   a processor configured to generate additional data as output by a machine-learned model in response to input of the suboptimal or corrupted data and the imager data, the processor configured to form an emission image from the suboptimal or corrupted data and the additional data; and
   a display configured to display the emission image.

15. The system of claim 14 wherein the suboptimal or corrupted data comprises data failing to satisfy a clinical guideline for scan quality or having a sampling at least 10% below Nyquist for at least a region of the patient.

16. The system of claim 14 wherein the processor is configured to select the machine-learned model from a plurality of machine-learned models.

17. The system of claim 16 wherein the processor is configured to apply the machine-learned models of the plurality to the suboptimal or corrupted data and select the machine-learned model to output the additional data based on the application.

18. The system of claim 14 wherein the machine-learned model comprises a deep learned neural network.

19. A method for training for rescue of medical information from an emission tomography scan by an emission tomography scanner, the method comprising:
   obtaining a plurality of ground truth emission tomography data;
   corrupting the emission tomography data by removing one or more views, sub-sampling, or truncating such that the emission tomography data is below a Nyquist rate for at least a part;
   machine training a network to generate the medical information from the corrupted emission tomography data based on the ground truth emission tomography data; and
   storing the machine-trained network.

20. The method of claim 19 further comprising machine training the network to generate the medical information from the corrupted emission tomography data and data from another modality of imaging.

* * * * *

UNITED STATES PATENT AND TRADEMARK OFFICE
CERTIFICATE OF CORRECTION

PATENT NO. : 11,151,759 B2
APPLICATION NO. : 16/564511
DATED : October 19, 2021
INVENTOR(S) : Alexander Hans Vija and Michal Cachovan Page 1 of 1

It is certified that error appears in the above-identified patent and that said Letters Patent is hereby corrected as shown below:

In the Specification

Column 2, Lines 26-27, "In a second aspect, a system is provided for recovering from an suboptimal..." should read "In a second aspect, a system is provided for recovering from a suboptimal..."

Column 3, Line 38, "... artifact reduction, noise reduction, an/or replacing..." should read "... artifact reduction, noise reduction, and/or replacing..."

Column 4, Lines 43-44, "Iterative reconstruction may be performed with some data missing..." should read "Iterative reconstruction may be performed when some data is missing..."

In the Claims

Column 14, Claim 13, Line 14, "... artificial corruption comprising the ground truth data." should read "... artificial corruption comprising ground truth data."

Signed and Sealed this
Second Day of August, 2022

Katherine Kelly Vidal
*Director of the United States Patent and Trademark Office*